US006960663B2

United States Patent
Kim et al.

(10) Patent No.: US 6,960,663 B2
(45) Date of Patent: Nov. 1, 2005

(54) PHENYL PYRIDINE-IRIDIUM METAL COMPLEX COMPOUNDS FOR ORGANIC ELECTROLUMINESCENT DEVICE, PROCESS FOR PREPARING THE COMPOUNDS, AND ORGANIC ELECTROLUMINESCENT DEVICE USING THE COMPOUNDS

(75) Inventors: Ki-Dong Kim, Daejeon (KR); Sang-Dae Kim, Daegu (KR); Yoon-Soo Han, Kyongsangbuk-do (KR); Yoon-Heung Tak, Gumi-shi (KR); Dong-Uk Kim, Daegu (KR); Tae-Jeong Kim, Daegu (KR); Ung-Chan Yoon, Busan (KR); Sung-Hoon Kim, Daegu (KR); Hee-Wan Moon, Daegu (KR)

(73) Assignee: LG Electronics, Inc., Seoul (KR)

( * ) Notice: Subject to any disclaimer, the term of this patent is extended or adjusted under 35 U.S.C. 154(b) by 0 days.

(21) Appl. No.: 10/724,766

(22) Filed: Dec. 2, 2003

(65) Prior Publication Data

US 2004/0249156 A1 Dec. 9, 2004

(30) Foreign Application Priority Data

Dec. 3, 2002 (KR) ........................ 2002-76208

(51) Int. Cl.$^7$ ............................. G11C 13/04; C07F 5/02
(52) U.S. Cl. ......................... 546/4; 365/110; 365/111; 514/277
(58) Field of Search ............................. 546/4; 514/277; 365/110, 111

(56) References Cited

PUBLICATIONS

C. Adachi et al., "Electroluminescence in Organic Films with Three–Layer Structure," Japanese Journal of Applied Physics, vol. 27, No. 2, Feb., 1988, pp. L269–L271.

C.W. Tang and S.A. VanSlyke, "Organic electroluminescent diodes," Appl. Phys. Lett., vol. 51(12), Sep. 21, 1987, pp. 913–915.

C. Adachi et al., "Organic electroluminescent device having a hole conductor as an emitting layer," Appl. Phys. Lett., vol. 55(15), Oct. 9, 1989, pp. 1489–1491.

M.A. Baldo et al., "High–efficiency fluorescent organic light–emitting devices using a phosphorescent sensitizer," Nature, vol. 403, Feb. 17, 2000, pp. 750–753.

*Primary Examiner*—Rita Desai
(74) *Attorney, Agent, or Firm*—Fleshner & Kim, LLP

(57) ABSTRACT

The present invention relates to luminescence materials for an organic electroluminescent device (OELD), and particularly to phenyl pyridine-iridium metal complex compounds of formula (1), and preparation method thereof. In addition, the present invention relates to an organic electroluminescent device using the luminescence materials according to the present invention, which can greatly enhance the efficiency of luminescence and increase the operating life time of the device:

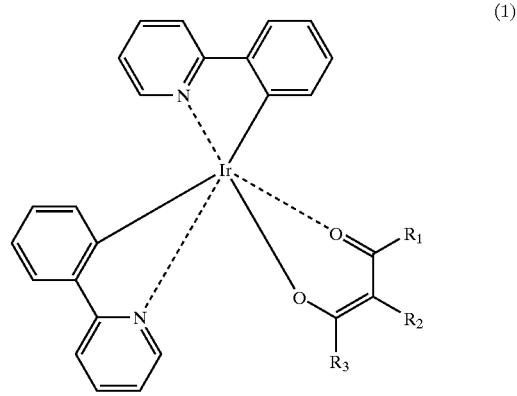

(1)

wherein $R_1$, $R_2$ and $R_3$ each are the same as defined in the specification.

7 Claims, 1 Drawing Sheet

PHENYL PYRIDINE-IRIDIUM METAL COMPLEX COMPOUNDS FOR ORGANIC ELECTROLUMINESCENT DEVICE, PROCESS FOR PREPARING THE COMPOUNDS, AND ORGANIC ELECTROLUMINESCENT DEVICE USING THE COMPOUNDS

FIELD OF THE INVENTION

The present invention relates to luminescence materials for an organic electroluminescent device (OELD), particularly to phenyl pyridine-iridium metal complex compounds represented by the following formula (1), and a preparation method thereof:

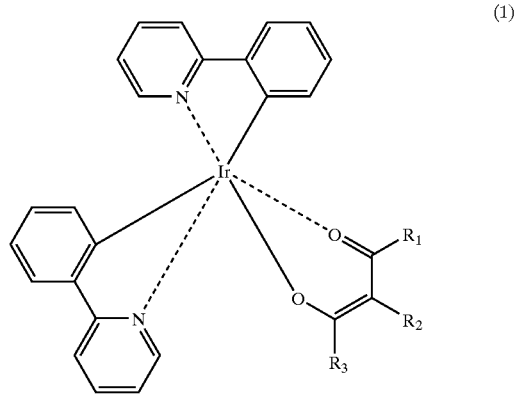

(1)

wherein $R_1$, $R_2$ and $R_3$ each are as defined below.

In addition, the present invention relates to an organic electroluminescent device using the luminescence materials according to the present invention, which device can greatly enhance the luminescence efficiency and increase the driving life time of the device.

BACKGROUND OF THE INVENTION

The field of display device is very important for the information and communication industry. Recently, more advanced performance in this field is asked for in accordance with the development of information and communication technology. Display can be divided into luminescent type and non-luminescent type. The luminescent type of display comprises Cathode Ray Tube (CRT), Electroluminescence Display (ELD), Light Emitting Diode (LED), Plasma Display Panel (PDP), etc. The non-luminescent type of display comprises Liquid Crystal Display (LCD), etc.

The luminescent and non-luminescent type of displays have such basic performances as operation voltage, consumption power, brightness, contrast, response rate, life time, etc. However, LCD that has been widely used up to now has some problems in the above basic performances in regard to response rate, contrast, and sight dependency. Thus, the LED-using display is anticipated to take the place of next-generation display device by solving the above LCD problems and by providing such many advantages as fast response speed, no need for back light due to self-emission, and excellent brightness.

However, LED is mainly used with a crystal form of inorganic material, and so is hard to be applied to a large size of electroluminescent device. In addition, the electroluminescent device using inorganic material needs more than 200 V of operation voltage and is very expensive. However, Eastman Kodak reported in 1987 that the company manufactured a device made with a material having $\pi$-conjugate structure such as alumina quinine, and thereafter, the electroluminescent device study using organic material has been more active.

The electroluminescence device (EL device, below) can be divided into inorganic EL device and organic EL device depending on what material is used to form the emission layer (emitter layer).

The organic EL device is a self-emitting type of device that electrically excites fluorescent organic compound, is superior to the inorganic EL device in brightness, operation voltage, and response rate, and also can emit multi-color.

In addition, the organic EL device is a luminescent device to emit in low voltage current, and has superior properties such as enhanced brightness, high speed of response, wide viewing angle, plane luminescence, slim type, and multi-color luminescence.

Thus, the organic EL device is expected to be applicable to a full-color plat panel display due to such superior properties that cannot be found in other displays.

C. W. Tang et al. reported the first practical device performance of the organic EL device in Applied Physics Letters, vol. 51 (12) pp 913–915 (1987). They developed a thin film (a hole transport layer) of laminated structure formed by diamine analogues as organic layer and a thin film (an electron transport layer) formed by tris(8-quinolinolate) aluminum (Alq3, below). The laminated structure can lower the injection barrier of electron and hole from both electrodes to the organic layer, and also can enhance the re-combination probability of electron and hole from the inner organic layer.

Later, C. Adachi et al. developed an organic EL device having an organic luminescent layer with three-laminated structure of hole transport layer, emission layer, and electron transport layer [Japanese Journal of Applied Physics, vol. 27 (2), pp L269–L271 (1988)], and two-laminated structure of hole transportable emission layer and electron transport layer [Applied Physics Letter, vol. 55 (15), pp 1489–1491 (1989)], and showed that the optimization of device property can be achieved by constructing a multi-layer structure suitable for materials and combination thereof.

The organic EL comprises a first electrode (anode), a second electrode (cathode), and organic luminescent media. This organic luminescent media have at least two separate organic luminescent layers, i.e. one layer to inject and transport electron, and the other layer to inject and transport hole into the device. In addition, another multi-layer of thin organic film can be involved. The above layers to inject and transport electron and hole each can be divided into an electron injection layer, an electron transport layer, a hole injection layer, and a hole transport layer. In addition, the organic luminescent media can further include an emission layer besides the above layers.

The simple structure of organic EL device comprises a first electrode/an electron transport layer, and an emission layer/a second electrode. In addition, the structure of organic EL device can be separated into a first electrode/a hole injection layer/a hole transport layer/an emission layer/an electron transport layer/an electron injection layer/a second electrode.

The operation principle of the organic EL device having the above structure is as follows.

If the voltage is applied to the anode and cathode, the hole injected from the anode is transferred to the emission layer via the hole transport layer. Meanwhile, the electron is injected from the cathode to the emission layer via the electron transport layer. The hole and electron are re-combined in the emission layer to form exiton. The exiton is changed from the excitation state to the basic state, and thereby the fluorescent molecule of the emission layer becomes luminescent to form images.

At present, the material conventionally used for the hole transport layer is triphenylamine analogues. In addition, organic metal complex compounds or heterocyclic compounds are used for the electron transport layer. Organic compounds or organic metal complex compounds are solely used for the emission layer or as host of the emission layer. When organic compounds or organic metal complex compounds are used as host of the emission layer, organic luminescent materials or organic luminescent materials of metal complex type are used as dopant to control the color of luminescence.

The maximum quantum efficiency of luminescent materials used in an organic EL device is about 5% by theoretical calculation. If such low quantum efficiency can be enhanced, the life time of the device can be increased. When the molecule is fallen from the monoplet excitation state to the basic state, it is called generally as fluorescence. On the other hand, when the molecule is fallen from the triplet excitation state to the basic state, it is called as phosphorescence. In case of fluorescence, the maximum efficiency emitted from the basic state of molecule is about 25%. In case of phosphorescence, that is about 75%. Therefore, the phosphorescence materials having high luminescence efficiency have been applied to an organic thin layer, especially the emission layer of organic EL device, but the suitable materials for the organic thin layer have not been developed.

One practical method for the full-color display is to develop a material having high luminescence efficiency for the organic thin layer, especially the emission layer of organic EL device. Thus, study has been made for iridium metal complex organic compounds as phosphorescence materials for the organic EL device. The organic EL device using Such material as dopant of the emission layer has known to show high luminescence efficiency at operation [see Nature, vol. 403, pp 750–753 (2000)].

Iridium metal complex organic compounds to constitute the emission layer have a different luminescent color in accordance with the molecular structure of ligand. In this case, the emission layer only comprises iridium metal complex organic compounds of phosphorescence materials or of phosphorescence materials as dopant. However, phosphorescence materials having practical luminescence efficiency have not been developed.

In view of the above, the present inventors have conducted intensive studies to develop novel phenyl pyridine-iridium metal complex compounds of formula (1) which have practical luminescence efficiency, and completed the present invention.

SUMMARY OF THE INVENTION

An object of the present invention is to provide novel phenyl pyridine-iridium metal complex compounds and preparation methods thereof.

Another object of the present invention is to provide an organic electroluminescent device having one or more organic thin layers formed between the first electrode and second electrode, wherein at least any one layer of the organic thin layers comprises one or more luminescence materials according to the present invention.

In order to accomplish these objects of the present invention, the present invention provides novel phenyl pyridine-iridium metal complex compounds represented by the following formula (1):

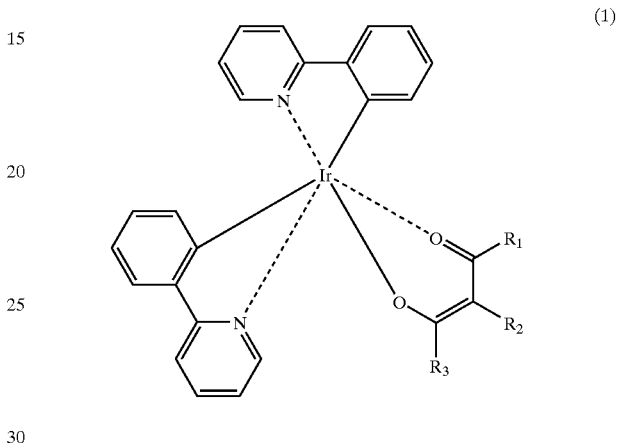

(1)

wherein, $R_1$, $R_2$ and $R_3$ each are independently a straight or branched alkyl group having 1 to 18, preferably 1 to 8, more preferably 1 to 4 carbon atoms, a cycloalkyl group having 5 to 18 carbon atoms, a substituted or un-substituted aromatic group having 5 to 18 carbon atoms, a heterocyclic aromatic group having 5 to 18 carbon atoms, and one or more hetero-atoms selected from the group consisting of N, O and S; or two or more of $R_1$, $R_2$ and $R_3$ taken together form a aliphatic cycle having 5 to 20 carbon atoms, an aromatic cycle having 5 to 20 carbon atoms, or a heterocyclic aromatic cycle having 5 to 20 carbon atoms, and one or more hetero-atoms selected from the group consisting of N, O and S.

The representative examples of formula (1) are described below. However, the present invention shall not be limited by the representative examples.

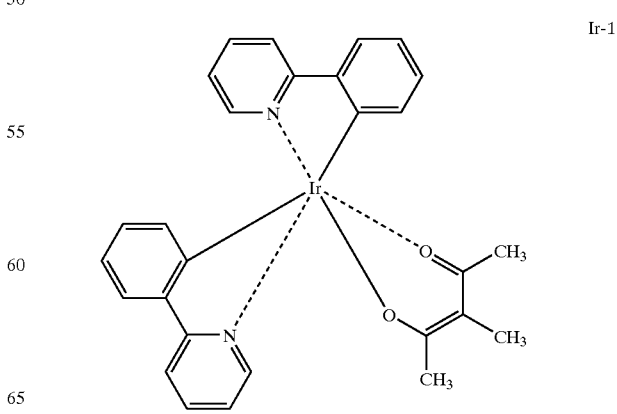

Ir-1

-continued

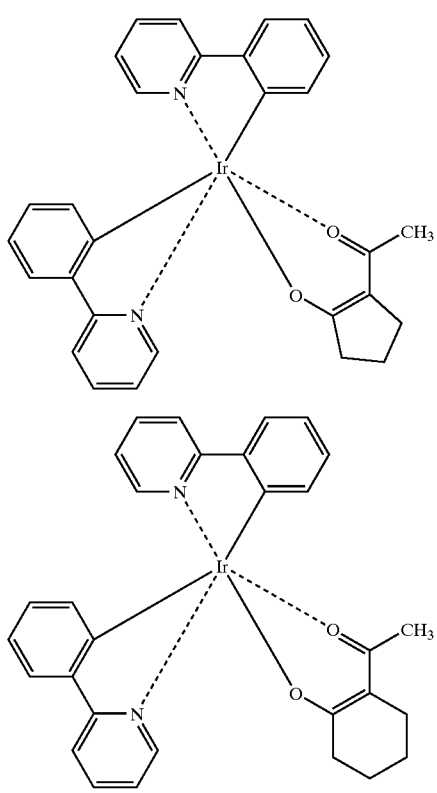

The substituents of the compounds of formula (1) may be substituted by a straight or branched alkyl group having 1 to 10 carbon atoms, or an alkoxy group having 1 to 10 carbon atoms, but not limited thereto.

The present invention also provides a preparation method of the compound of formula (1).

The compound of formula (1) can be prepared by:
1) reacting the phenyl pyridine compound of formula (1) below with $IrCl_3*xH_2O$ or $Na_3IrCl_6*xH_2O$ to form a precursor of the compound of formula (1); and
2) reacting the precursor obtained by above step 1) with the compound of formula (3) below to obtain the desirable compound of formula (1):

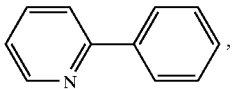

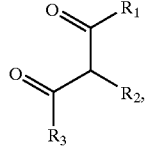

wherein, $R_1$, $R_2$ and $R_3$ each are as defined above.

The reaction temperature of above step 1) in the preparation method is 0° C. to 140° C., preferably 100° C. to 135° C., and the reaction time is 1 to 240 hours, preferably 10 to 48 hours. The conventional organic solvent, preferably alcoholic derivatives, more preferably 2-ethoxy ethanol, can be used as the reaction solvent. The molar ratio of phenyl pyridine compound of formula (2) to iridium complex compound can be 0.0001 to 10, preferably 0.1 to 1.

The reaction temperature of above step 2) is 0° C. to 140° C., preferably 100° C. to 135° C., and the reaction time is 1 to 240 hours, preferably 10 to 48 hours. The conventional organic solvent, preferably alcoholic derivatives, more preferably 2-ethoxy ethanol, can be used as the reaction solvent. The molar ratio of a precursor compound of iridium complex compound obtained by above step 1 to the compound of formula (3) can be 0.01 to 100, preferably 0.1 to 10. Alkaline substances, such as metal oxides, metal hydroxides, metal carbonates, preferably metal carbonates, more preferably $K_2CO_3$, can be used to accelerate the reaction.

In addition, the present invention provides an organic EL device comprising the compound of formula (1), more specifically, to an organic EL device having one or more organic thin layers formed between the first electrode and second electrode, wherein at least any one layer of the organic thin layers comprises one or more luminescence materials according to the present invention.

The compound of formula (1) can be used alone, in a type of combination, or as host doped by other materials, to any of the organic thin layers, or used as dopant to the other hole transport material, emission material, or electron transport material. Preferably, the compound of the present invention can be used alone or as dopant to the emission layer.

A variety of embodiments of the organic EL device using the luminescence materials of the present invention can be achieved. Basically, the emission layer, if necessary, is introduced into the pair of electrodes (anode and cathode). Then, if necessary, a hole injection layer and/or a hole transport layer and/or an electron injection layer and/or an electron transport layer can be introduced. More specifically, the structure examples of the device are: (1) anode/emission layer/cathode; (2) anode/hole transport layer/emission layer/cathode; (3) anode/hole transport layer/electron transport layer/cathode; (4) anode/hole injection layer/hole transport layer/emission layer/cathode; (5) anode/hole injection layer/hole transport layer/emission layer/electron transport layer/cathode; (6) anode/hole injection layer/hole transport layer/emission layer/electron transport layer/electron injection layer/cathode; (7) anode/hole injection layer/emission layer/electron injection layer/cathode; and (8) anode/hole transport layer/emission layer/hole blocking layer/electron transport layer/electron injection layer/cathode, etc. If necessary, the device having the above structures is supported by a substrate. No particular limitation exists for the substrate, and the conventionally substrate used in the organic EL device, such as glass, transparent plastics, quartz, etc., can be used.

Each layer constructing the organic EL device of the present invention can be formed by applying the comprising materials under the conventional methods such as deposition method, spin-coat method, or cast method to laminate the layers.

No particular limitation exists on the thickness of each layer, such as emission layer, formed by such method, and a suitable selection may be made by conditions of the device.

In addition, for the anode of the organic EL device, a metal having work function more than 4.0 eV, alloy, electric-conductive compound, or combination thereof can be used as electrode. The example of such electrode material is electric conductive transparent or non-transparent material, such as ITO, $SnO_2$, ZnO, Au, etc. The anode can be manufactured by forming a thin film through the method of deposition, sputtering, etc.

Besides, for the cathode of the organic EL device, a metal having work function less than 4.2 eV, alloy, electric-conductive compound, or combination thereof can be used as electrode. The examples of such electrode material are calcium, magnesium, lithium, aluminum, magnesium alloy, lithium alloy, aluminum alloy, aluminum/lithium mixture, magnesium/silver mixture, indium, etc. The cathode also can be manufactured by forming a thin film through the method of deposition, sputtering, etc.

Preferably, the sheet resistance as electrode is less than several hundreds Ω/mm, and the thickness of film is selected from the range of 10 nm to 1 μm, preferably 50 to 200 nm.

For the organic EL device of the present invention, it is preferable to make each of, or both anode and cathode transparent or semi-transparent, and transmit the luminescence through the anode or cathode to enhance the transmission effect of the luminescence.

For other materials for hole injection layer and hole transport layer in the organic EL device of the present invention can be used any material conventionally used as hole transport material among photo-conductive materials, and any random material among known materials used as hole injection layer or hole transport layer.

For the organic EL device of the present invention, an electron transport layer comprises an electron transport compound, and has a role to transport electron injected from the cathode to the emission layer. No particular limitation exists for such electron transport compound, and any known conventional compound can be selected thereas.

Below, one embodiment for suitable methods to manufacture the organic EL device of the present invention having above (8) structure is explained as follows:

(1) a first electrode, ITO, is formed on a transparent substrate with the thickness of about 10~1,000 nm;

(2) a hole transport layer is formed thereon by using NPD (N,N'-dinaphthyl-N,N'-phenyl-(1,1'-biphenyl)-4,4'-diamine) with the thickness of about 1 nm~200 nm;

(3) then, an organic emission layer is deposited thereon by using CBP (4,4'-Bis(carbazole-9-yl)-biphenyl) with the thickness of about 1 nm 200 nm [a compound of formula (1) is added as dopant by about 0.01%~40%];

(4) a hole blocking layer is formed on the emission layer by using BCP (2,9-Dimethyl-4,7-diphenyl-1,10-phenanthroline) with the thickness of about 1 nm~200 nm;

(5) an electron transport layer is deposited thereon by using Alq3 (tris(8-hydroxy-quinolate)aluminum) with the thickness of about 1 nm~200 nm;

(6) then, an electron injection layer comprising alkaline metal or alkaline earth metal compound is formed in the thickness of about 0.1 nm~200 nm; and (7) a second electrode comprising Mg/Ag with the thickness of about 10 nm~1000 nm is laminated.

BRIEF DESCRIPTION OF THE DRAWINGS

The present invention will be more clearly understood from the detailed description in conjunction with the following drawings.

DETAILED DESCRIPTION OF THE INVENTION

Figure 1:
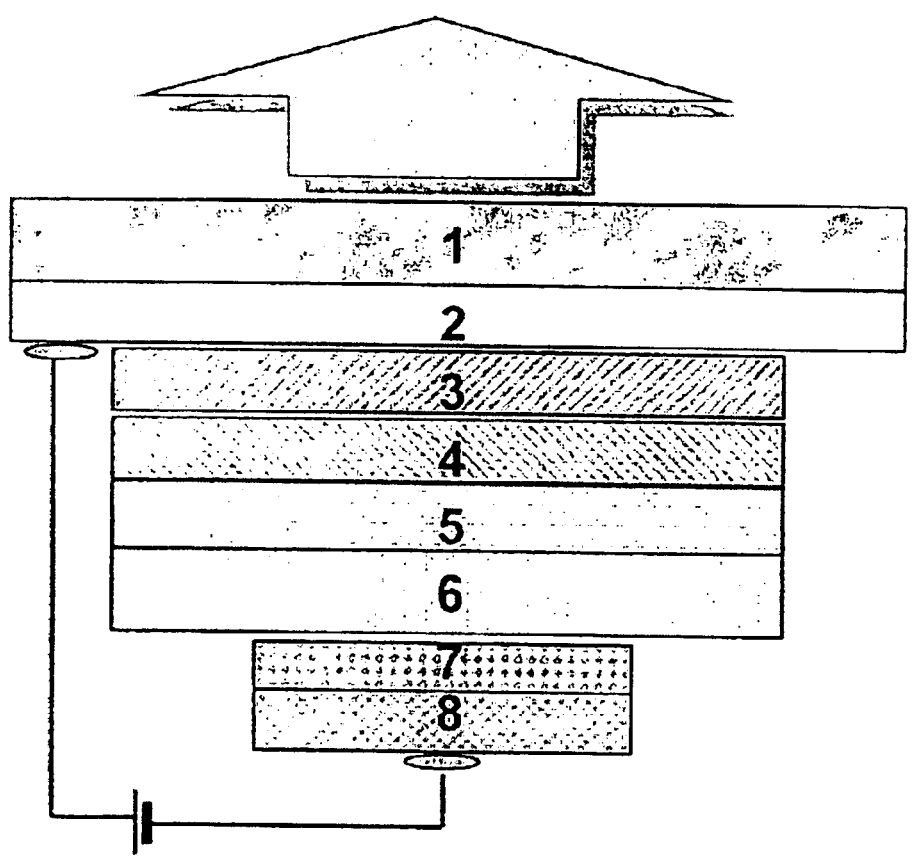
FIG. 1 is a schematic sectional view of the conventional organic EL device.

The synthetic examples of the compounds of formula (1) of the present invention, and the organic EL device applied with the compounds are explained through the synthetic examples and practicing examples below. Additional advantages, objects, and features of the present invention will be set forth in the description which follows and will also become apparent to those who practice the present invention. The objectives and other advantages of the present invention will be explained in the written description including the claims.

SYNTHETIC EXAMPLES

Synthetic Example 1

(1) Synthesis of the Precursor Compound of Iridium Complex Compound, 1

Phenyl pyridine (1408 mg, 9.07 mmol) and $IrCl_3 \cdot 3H_2O$ (800 mg, 2.27 mmol) were added to 100 ml of a reaction vessel and 30 ml of purified solvent, and 2-ethoxy ethanol was added thereto under a flow of nitrogen gas, and then the mixture was mixed at room temperature for 6 hours and refluxed at 100° C. for 12 hours. The mixture was fallen down to room temperature, and filtrated with G4 size of glass filter, and the precipitate was washed with MeOH (15 ml) three times. The precipitate was dissolved by adding $CH_2Cl_2$ to the glass filter, and the dissolving solution was collected, and then evaporated by a distillation apparatus in vacuum. The resulting material was purified with column chromatography to obtain 700 mg of the precursor of iridium complex compound, 1 (yield: 58%).

(2) Synthesis of Iridium Complex Compound (Ir-1)

The precursor compound synthesized above [Synthetic Example 1], 1 (50 mg, 0.0467 mmol) and 3-methyl-2,4-pentandione (53.3 mg, 0.467 mmol), and $K_2CO_3$ (50 mg) were added to 50 ml of a reaction vessel, and 10 ml of purified solvent, 2-ethoxy ethanol, was added thereto under a flow of nitrogen gas, and refluxed at 100° C. for 1 hour. The temperature of this mixture was fallen down to room temperature, and the mixture was filtrated with G4 size of glass filter, and the precipitate was washed with MeOH (15 ml) three times. The precipitate was dissolved by adding $CH_2Cl_2$ to the glass filter, and the dissolving solution was collected, and then evaporated by a distillation apparatus in vacuum. The resulting material was purified with column chromatography to obtain 55 mg of desired compound, Ir-1 (yield: 96%).

(3) Analysis of Ir-1 Compound

The molecular structure of the material obtained above was analyzed by using $^1$NMR and mass analyzer, and from the result of analysis, it was confirmed that Ir-1 was synthesized.

$^1$H NMR (CDCl3)): δ 8.5(d, 2H), 7.8(d, 2H), 7.7(t, 2H), 7.5(d, 2H), 7.1(t, 2H), 6.8(t, 2H), 6.7(t, 2H), 6.2(t, 2H), 2.1(s, 3H), 1.8(s, 6H)

Mass: calculated value—614.15; experimental value—614.25

The preparation steps of above Ir-1 compound are summarized below, and other compounds including formula (1) are synthesized by a similar method to Synthetic Example 1.

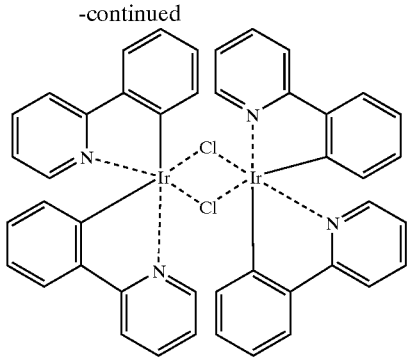

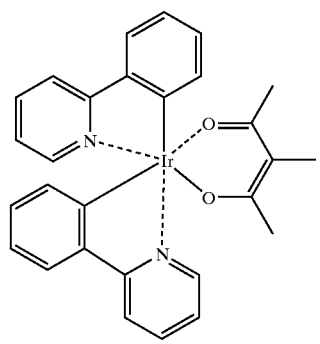

Ir-1

The synthesized materials as above were further purified with a vacuum sublimation apparatus to use in the organic EL device.

Example 1

For the present example, the organic EL device using Ir-1 as dopant and CBP as host of green uminescence was manufactured. First, a hole transport layer was formed with the thickness of 50 nm by depositing NPD (N,N'-dinaphthyl-N,N'-phenyl-(1,1'-biphenyl)-4,4'-diamine) in vacuum on an ITO-deposited glass, washed by a microwave. Then, an emission layer is formed with the thickness of 30 nm on the hole transport layer by depositing CBP (host), which was doped with Ir-1 (dopant) by 1.0%. A hole blocking layer (BCP; 5 nm), an electron transport layer (Alq3; 40 nm), an electron injection layer ($Li_2O$; 25 nm), and a cathode (Mg/Ag; 100 nm) were formed in order thereon by depositing in vacuum to complete the organic EL device.

The direct voltage of forward bias was applied to the organic EL device manufactured by Example 1, and luminescent property thereof was evaluated. The luminescent color was green. As a result of spectroscopy, a spectrum having approximately 530 nm of luminescent peak was obtained. In addition, as a result of voltage-brightness test, 5,000 $cd/m^2$ of brightness at 8.2V was obtained, at which point the efficiency was 14 lm/W (see Table 1).

Example 2

For the present example, the organic EL device using Ir-2 as dopant and CBP as host of green luminescence was manufactured. At first, a hole transport layer was formed with the thickness of 50 nm by depositing NPD (N,N'-dinaphthyl-N,N'-phenyl-(1,1'-biphenyl)-4,4'-diamine) in vacuum on an ITO-deposited glass, washed by a microwave. Then, an emission layer is formed with the thickness of 30 nm on the hole transport layer by depositing CBP (host), which was doped with Ir-2 (dopant) by 1.0%. A hole blocking layer (BCP; 5 nm), an electron transport layer (Alq3; 40 nm), an electron injection layer ($Li_2O$; 25 nm), and a cathode (Mg/Ag; 100 nm) were formed in order thereon by depositing in vacuum to complete the organic EL device.

The direct voltage of forward bias was applied to the organic EL device manufactured by Example 2, and luminescent property thereof was evaluated. The luminescent color was green. As a result of spectroscopy, a spectrum having approximately 525 nm of luminescent peak was obtained. In addition, as a result of voltage-brightness test, 5,000 $cd/m^2$ of brightness at 6.8V was obtained, at which point the efficiency was 13 lm/W (see Table 1).

Comparative Example 1

An organic EL device was manufactured by the same method as Examples 1 and 2 except using Ir(ppy)3 (Iridium (III) tris(2-phenylpyridine)) as dopant.

The direct voltage of forward bias was applied to the organic EL device manufactured by Comparative Example 1, and luminescent property thereof was evaluated. The luminescent color was green. As a result of spectroscopy, a spectrum having approximately 510 nm of luminescent peak was obtained. In addition, as a result of voltage-brightness test, 5,000 $cd/m^2$ of brightness at 9.8V was obtained, at which point the efficiency was 5.3 lm/W (see Table 1).

TABLE 1

| | Host | Dopant | Applied Voltage (V) | Brightness ($cd/m^2$) | Efficiency (lm/W) | Spectrum (nm) |
|---|---|---|---|---|---|---|
| Example 1 | CBP | Ir-1 | 8.2 | 5,000 | 14 | 530 |
| Example 2 | CBP | Ir-2 | 6.8 | 5,000 | 13 | 525 |
| Comparative Example 1 | CBP | Ir(ppy)$_3$ | 9.8 | 5,000 | 5.3 | 510 |

As shown in the above results, when iridium complex compound was used as dopant, not in accordance with the present invention, it is apparent that the efficiency was greatly reduced. In addition, the organic EL device using the novel phenyl pyridine-iridium complex compound of formula (1) according to the present invention can achieve practical luminescence efficiency and enhanced operating life time and stability.

It will be apparent to those skilled in the art that various modifications and variations can be made for the present invention. Therefore, it is intended that the present invention covers the modifications and variations of this invention that come within the scope of the appended claims, and their equivalents.

What is claimed is:

1. A compound represented by the following formula (1):

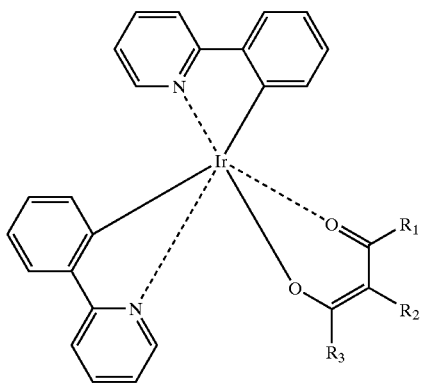

(1)

wherein $R_1$, $R_2$ and $R_3$ each are independently a straight or branched alkyl group having 1 to 18 carbon atoms, a cycloalkyl group having 5 to 18 carbon atoms, a substituted or un-substituted aromatic group having 5 to 18 carbon atoms, or two or more of $R_1$, $R_2$ and $R_3$ taken together form an aliphatic cycle having 5 to 20 carbon atoms, or an aromatic cycle having 5 to 20 carbon atoms.

2. The compound according to claim 1, wherein the compound is Ir-1, Ir-2, or Ir-3.

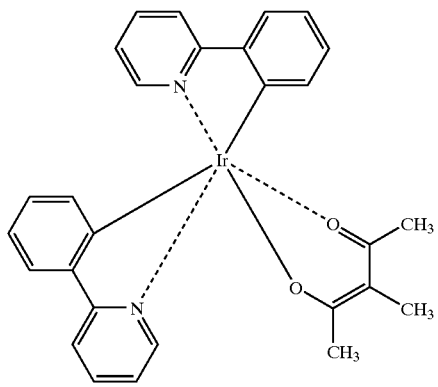

Ir-1

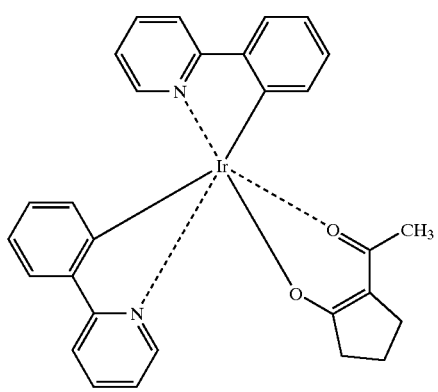

Ir-2

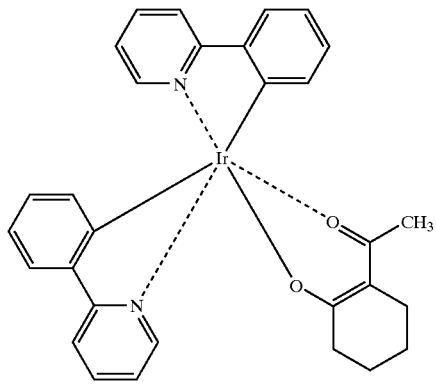

Ir-3

3. A preparation method of the compound of formula (1) comprising the steps of:

1) reacting the phenyl pyridine compound of formula (2) below with $IrCl_3 * xH_2O$ or $Na_3IrCl_6 * xH_2O$ to form a precursor compound of the formula:

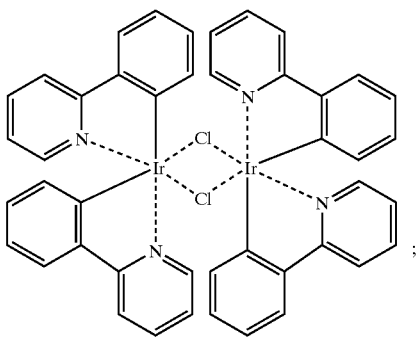

; and;

2) reacting the precursor compound obtained by the above step 1) with the compound of formula (3) below to obtain the compound of formula (1):

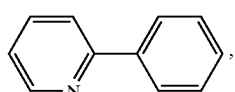

(2)

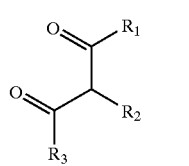

(3)

wherein $R_1$, $R_2$ and $R_3$ each are the same as defined in claim 1.

4. An organic electroluminescent device having one or more organic thin layers formed between a first electrode and a second electrode, wherein at least any one layer of the organic thin layers comprises one or more compounds represented by the formula (1) according to claim 1 or 2.

5. The organic electroluminescent device according to claim 4, wherein the organic thin layer comprises one or more layer selected from the group consisting of a hole transport layer, an emission layer, a hole blocking layer, an electron transport layer, and an electron injection layer.

6. The organic electroluminescent device according to claim 5, wherein at least one or more compounds represented by the formula (1) are used as dopant of the emission layer.

7. The organic electroluminescent device according to claim 5, wherein at least one or more compounds represented by the formula (1) are used as host of the emission layer.

* * * * *